United States Patent
Rozov et al.

(10) Patent No.: US 6,987,204 B2
(45) Date of Patent: Jan. 17, 2006

(54) PROCESS FOR RECOVERY OF 1,1,1,3,3,3-HEXAFLUOROISOPROPANOL FROM THE WASTE STREAM OF SEVOFLURANE SYNTHESIS

(75) Inventors: Leonid A. Rozov, Fair Lawn, NJ (US); Ralph A. Lessor, New Providence, NJ (US)

(73) Assignee: Baxter International Inc., Deerfield, IL (US)

( * ) Notice: Subject to any disclaimer, the term of this patent is extended or adjusted under 35 U.S.C. 154(b) by 54 days.

(21) Appl. No.: 10/755,850

(22) Filed: Jan. 12, 2004

(65) Prior Publication Data

US 2004/0147779 A1 Jul. 29, 2004

Related U.S. Application Data

(60) Provisional application No. 60/439,942, filed on Jan. 14, 2003.

(51) Int. Cl.
*C07C 41/09* (2006.01)
*C07C 41/42* (2006.01)

(52) U.S. Cl. .................... 568/682; 568/683; 568/684; 568/698; 568/842

(58) Field of Classification Search ............... 568/682, 568/683, 684, 698, 842
See application file for complete search history.

(56) References Cited

U.S. PATENT DOCUMENTS

| | | | |
|---|---|---|---|
| 3,476,860 A | 11/1969 | Croix et al. | |
| 3,527,814 A | 9/1970 | Croix et al. | |
| 4,250,334 A | 2/1981 | Coon et al. | |
| 5,233,098 A | * 8/1993 | Nakazora et al. | 568/842 |
| 5,811,596 A | * 9/1998 | Kawai et al. | 568/683 |
| 5,886,239 A | 3/1999 | Kudzma et al. | |
| 5,990,359 A | 11/1999 | Ryan et al. | |
| 6,100,434 A | 8/2000 | Bieniarz et al. | |
| 6,469,219 B1 | * 10/2002 | Khrimian et al. | 568/683 |

FOREIGN PATENT DOCUMENTS

WO  WO 02/50003 A1  6/2002
WO  WO 02/50005 A1  6/2002

OTHER PUBLICATIONS

Kudzma et al., Diisopropylethylamine mono(hydrogen fluoride) for Nucleophilic . . . , Journal of Fluorine Chemistry, 2001, 11–16, vol. 111.

* cited by examiner

*Primary Examiner*—Rodalynd Keys
(74) *Attorney, Agent, or Firm*—Michael G. Mayo; Andrew G. Kolomayets

(57) ABSTRACT

Provided is a process of obtaining 1,1,1,3,3,3-hexafluoro-2-propanol ("HFIP") from a composition comprising an HFIP hydrolyzable precursor. The HFIP hydrolyzable precursor is a compound, other than sevoflurane itself, that has an intact 1,1,1,3,3,3-hexafluoroisopropoxy moiety[$(CF_3)_2CHO$—], and contains one or more moieties susceptible to acidic hydrolysis, such that HFIP is released upon such treatment. The process is useful, among other things, for recovering HFIP from waste streams associated with the synthesis of the inhalation anesthetic, fluoromethyl 2,2,2-trifluoro-1-(trifluoromethyl)ethyl ether ("sevoflurane"). The process includes heating the composition with a strong protic acid to a temperature effective to hydrolyze at least some of the HFIP hydrolyzable precursor to HFIP, and then isolating the HFIP from the heated composition.

15 Claims, No Drawings

PROCESS FOR RECOVERY OF 1,1,1,3,3,3-HEXAFLUOROISOPROPANOL FROM THE WASTE STREAM OF SEVOFLURANE SYNTHESIS

CROSS REFERENCE TO RELATED APPLICATIONS

This application claims the benefit of U.S. Provisional Application No. 60/439,942, filed Jan. 14, 2003, the disclosure of which is hereby incorporated by reference in its entirety.

The present invention relates to a process of recovering of 1,1,1,3,3,3-hexafluoro-2-propanol ("HFIP") from waste streams associated with the synthesis of the inhalation anesthetic, fluoromethyl 2,2,2-trifluoro-1-(trifluoromethyl) ethyl ether ("sevoflurane").

In recent years, fluorinated ethers such as sevoflurane have been discovered which have useful anesthetic properties. Sevoflurane is an advantageous inhalation anesthetic because it provides for rapid onset of anesthesia and rapid recovery. Sevoflurane is administered by the inhalation route to warm-blooded animals in an amount of from about 1% to 5% by volume in admixture with oxygen or a gaseous mixture containing oxygen in an amount sufficient to support respiration.

Many of the preferred commercial processes for the preparation of sevoflurane rely on the use of the chemical intermediate HFIP as a starting material. For example, a preferred process for preparing sevoflurane consists of the three-step process that is depicted in Scheme 1. In the first step, reaction of HFIP with dimethyl sulfate in the presence of base provides methyl 2,2,2-trifluoro-1-(trifluoromethyl) ethyl ether ("sevomethyl ether") in high yields. Second, sevomethyl ether is treated in a photochemical chlorination procedure to provide chloromethyl 2,2,2-trifluoro-1-(trifluoromethyl)ethyl ether ("chlorosevo"). In the third step, the chlorosevo from the second step is reacted with a nucleophilic fluoride source, such as a tertiary amine hydrofluoride salt, to displace of the chlorine with fluoride ion, and provide sevoflurane as disclosed in U.S. Pat. No. 5,886,239 (the synthetic methods therein hereby incorporated by reference).

Scheme 1

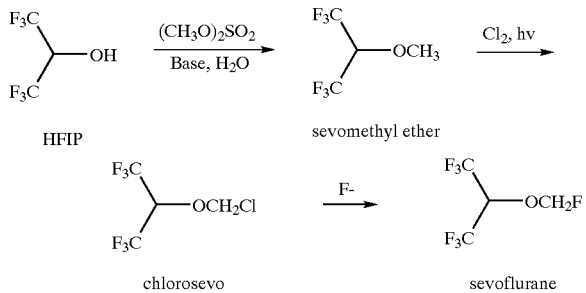

While the process described above provides high yields of sevoflurane, improvements to the overall process are desirable. In particular, loss of useful chemical intermediate in the conversion of sevomethyl ether to chlorosevo contributes to an inefficiency of the process. The conversion is a free radical process that generates unwanted chemical species. For instance, the chlorination process yields, in addition to the desired chlorosevo, unreacted sevomethyl ether and over-chlorinated species such as dichloromethyl 2,2,2-trifluoro-1-(trifluoromethyl)ethyl ether ("dichlorosevo").

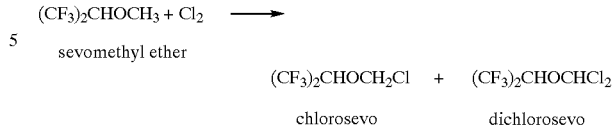

In addition, distillation of the crude reaction product to obtain the purified chlorosevo can also contribute to losses in the overall yield of the process. For instance, analysis of the waste stream (i.e., the stillpot residue) from the distillation reveals in addition to chlorosevo and dichlorosevo, a number of other high-boiling components such as di-(1,1,1,3,3,3-hexafluoroisopropyl)acetal (referred to herein as "di-HFIP acetal") shown below.

[(CF$_3$)$_2$CHO]$_2$CH$_2$ di-HFIP acetal

In addition, other components in the stillpot residue show an intact 1,1,1,3,3,3-hexafluoroisopropoxy moiety.

Other chemical processes used in the preparation of sevoflurane that rely on the use of HFIP are disclosed, for example, in U.S. Pat. No. 5,990,359 ("the '359 patent") and PCT publication WO 02/50003 (the processes description both hereby incorporated by reference). These processes combine HFIP with bis(fluoromethyl) ether in the presence of an acid to form sevoflurane. The '359 patent discloses that an acetal having the chemical formula (CF$_3$)$_2$CHOCH$_2$OCH$_2$F is produced as a by-product of the process. In addition to the aforementioned by-product acetal, WO 02/50003 describes the formation of di-HFIP acetal as another by-product of the process. The formation of these by-products consumes equivalents of HFIP at the expense of the desired product sevoflurane, and reduces the efficiency of the sevoflurane preparative process.

Another process for synthesizing sevoflurane is disclosed in U.S. Pat. No. 4,250,334 ("the '334 patent," the process description hereby incorporated by reference). The '334 patent discloses the reaction of HFIP with formaldehyde (including polymeric forms such as paraformaldehyde and 1,3,5-trioxane) and hydrogen fluoride. This conversion is typically conducted in the presence of a dehydrating agent such as concentrated sulfuric acid. The example of the '334 patent discloses the presence of formal- and acetal-containing by-products in addition to sevoflurane and HFIP in fractions distilled from the crude reaction mixture.

Similarly, U.S. Pat. No. 5,811,596 ("the '596 patent, the process description hereby incorporated by reference) discloses, among other things, the formation of polyethers of the general formula R$^1$O(CH$_2$O)$_n$R$^2$ where R$^1$ and R$^2$ are independently hydrogen, C$_1$–C$_{10}$ alkyl or haloalkyl groups, n is an integer from 1 to 10, and both of R$^1$ and R$^2$ are not hydrogen at the same time. It is disclosed that the polyethers can be formed as a by-product in the reaction of HFIP, formaldehyde and hydrogen fluoride in the presence of a dehydrogenator (e.g., sulfuric acid) to prepare sevoflurane. Other methods for the production of such polyethers are also disclosed in the '596 patent.

U.S. Pat. No. 6,100,434 ("the '434 patent," the process description hereby incorporated by reference) discloses the preparation of sevoflurane by a two-step method. In the first step, HFIP is combined with a quantity of either 1,3,5-trioxane or paraformaldehyde, in the presence of a chlorinating agent such as aluminum trichloride to produce chlorosevo. The resulting chlorosevo is then combined with a fluoride reagent (i.e., an alkali metal fluoride) to provide sevoflurane. Example 1 of the '434 patent describes the presence of a significant proportion (i.e., 22%) of di-HFIP acetal, in addition to chlorosevo, HFIP and polyketals in the crude reaction product.

As a significant component of the total manufacturing cost for sevoflurane is based on the material cost for HFIP, processes that allow for more efficient use of HFIP are desirable. For instance, processes that allow recovery of HFIP from waste streams containing mixtures of by-products formed in the synthesis of sevoflurane are needed. In addition, reductions in the volume of waste streams emanating from the sevoflurane synthetic processes, particularly halogenated waste streams can further reduce the cost of preparing sevoflurane.

SUMMARY OF THE INVENTION

In one aspect, the invention relates to a process of obtaining HFIP from a composition containing an HFIP hydrolyzable precursor. The process includes heating the composition with a strong protic acid to a temperature effective to hydrolyze at least some of the HFIP hydrolyzable precursor to HFIP, and then isolating the HFIP from the heated composition.

In another aspect, the invention relates to a process for preparing sevoflurane. The process includes:
 (a) reacting an HFIP feed in one or more reactions that provide sevoflurane and an HFIP hydrolyzable precursor;
 (b) separating the HFIP hydrolyzable precursor from the at least one of the one or more reactions of (a);
 (c) heating the separated HFIP hydrolyzable precursor with a strong protic acid at a temperature effective to convert the HFIP hydrolyzable precursor to HFIP; and
 (d) isolating the recovered HFIP.

In some embodiments, the process includes: (e) adding the recovered HFIP to the HFIP feed of (a).

In some embodiments of the process, steps (c) and (d) are conducted simultaneously.

The HFIP hydrolyzable precursor typically is one or more compounds selected from:

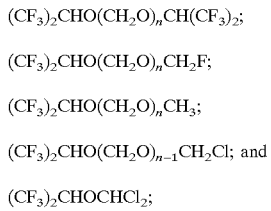

where n is independently an integer from 1 to 10.

In one embodiment of the process, step (a) can be conducted by treating the HFIP feed with formaldehyde and hydrogen fluoride to provide sevoflurane and the hydrolyzable HFIP precursor.

In an alternative embodiment, step (a) can be conducted by treating the HFIP feed with bisfluoromethyl ether to provide sevoflurane and the hydrolyzable HFIP precursor.

In another embodiment, step (a) is conducted by:
 (1) treating HFIP with a reactant selected from paraformaldehyde and 1,3,5-trioxane in the presence of a chlorinating agent to provide chlorosevo and the HFIP hydrolyzable precursor; and
 (2) treating chlorosevo with a fluoride reagent to give sevoflurane.

In yet another embodiment, step (a) can be conducted by treating the HFIP feed with a methylating agent to give sevomethyl ether, chlorinating the sevomethyl ether to give chlorosevo and the HFIP hydrolyzable precursor, and treating chlorosevo with a fluoride reagent to give sevoflurane.

In another aspect, the invention relates to a process for preparing chlorosevo from HFIP, including:
 (a) alkylating an HFIP feed to give sevomethyl ether;
 (b) chlorinating sevomethyl ether to give a mixture comprising chlorosevo and other HFIP hydrolyzable precursors (e.g., di-HFIP acetal and dichlorosevo);
 (c) isolating chlorosevo from the mixture to provide a chlorosevo-depleted mixture;
 (d) heating the chlorosevo-depleted mixture with a strong protic acid at a temperature effective to convert the other HFIP hydrolyzable precursors to HFIP; and
 (e) isolating recovered HFIP from the chlorosevo-depleted mixture.

In some embodiments, the process includes: (f) adding the recovered HFIP to the HFIP feed of (a), and repeating (a) through (e). The overall process can be conducted as a serial or continuous process for producing chlorosevo by repeating (a) through (f).

In some embodiments, the process further includes isolating sevomethyl ether from the mixture of (b) or the chlorosevo-depleted mixture of (c).

In certain embodiments of the process, the strong protic acid in (c) is selected from the group consisting of sulfuric acid, benzenesulfonic acid, toluenesulfonic acid, methanesulfonic acid, hydrochloric acid, phosphoric acid and polyphosphoric acid. A preferred strong protic acid is concentrated sulfuric acid. Where sulfuric acid is used in the hydrolysis of (c), the chlorosevo-depleted mixture is preferably heated with at least 10% by volume of concentrated sulfuric acid.

In some embodiments of the process for preparing chlorosevo, step (d) is conducted at atmospheric pressure. In such embodiments, the temperature to which the chlorosevo-depleted mixture is heated with a strong protic acid is preferably at least 60° C.

The isolation of chlorosevo in (c) can be conducted by distillation of the mixture, and isolation of distilled chlorosevo. In certain embodiments, the isolation can further include isolation of unreacted sevomethyl ether, in addition to chlorosevo. The isolation can be conducted by fractional distillation with isolation of chlorosevo and unreacted sevomethyl ether in separate distillation fractions.

Definitions

The following terms shall have, for the purposes of this application, the respective meanings set forth below.

"HFIP hydrolyzable precursor" means a compound, other than sevoflurane itself, that has an intact 1,1,1,3,3,3-hexafluoroisopropoxy moiety[$(CF_3)_2CHO$—], and contains one or more moieties susceptible to acidic hydrolysis such that HFIP is released upon such treatment.

DETAILED DESCRIPTION OF THE INVENTION

The present invention relates to a process of recovering of HFIP from waste streams produced in the synthesis of sevoflurane. Using the method of the invention, the cost effectiveness of sevoflurane synthetic processes are improved by the recovery of a valuable material and by the reduction in the volume of the waste stream in sevoflurane synthetic processes.

In one embodiment, the invention relates to a process for preparing sevoflurane that includes reacting an HFIP feed in one or more reactions that provide sevoflurane and an HFIP hydrolyzable precursor. HFIP hydrolyzable precursors contain an intact 1,1,1,3,3,3-hexafluoroisopropoxy moiety and one or more moieties susceptible to acidic hydrolysis such that HFIP is released upon such treatment. HFIP hydrolyzable precursors can therefore be viewed as a source of HFIP, that can then be tapped through acidic hydrolysis.

The process also includes separating the HFIP hydrolyzable precursors from the one or more reactions that provide sevoflurane. Such separation includes isolating purified sevoflurane or a desired precursor of sevoflurane (e.g., chlorosevo) to leave crude reaction mixtures containing HFIP hydrolyzable precursors. The separated HFIP hydrolyzable precursors are heated with a strong protic acid at a temperature effective to convert the HFIP hydrolyzable precursors to HFIP, and thereafter, the HFIP is isolated by, for example, distillation.

The HFIP hydrolyzable precursors can arise as discussed above in association with several different processes for the preparation of sevoflurane that employ HFIP as a chemical intermediate. For example, in some processes such HFIP hydrolyzable precursors can arise as by-products that are formed in reactions that directly yield sevoflurane or in reactions that give chemical intermediates used in preparing sevoflurane as described above. In some instances, HFIP hydrolyzable precursors can arise through reaction of one or more equivalents of formaldehyde (or paraformaldehyde or 1,3,5-trioxane or the like) with HFIP. These by-products can also form as a result of thermal or hydrolytic processes that can occur during purification steps such as distillation.

HFIP hydrolyzable precursors share an intact hexafluoroisopropyloxy moiety, and one or more moieties that are susceptible to acidic hydrolysis. Such hydrolyzable moieties include acetals, ketals, hemiacetals, hemiketals, α-halomethyl ethers, α,α-dihalomethyl ethers and the like. HFIP hydrolyzable precursors include, for example:

$(CF_3)_2CHO(CH_2O)_nCH(CF_3)_2$ where n is an integer from 1 to 10, in particular n=1;

$(CF_3)_2CHO(CH_2O)_nCH_2F$ where n is an integer from 1 to 10, in particular n=1;

$(CF_3)_2CHO(CH_2O)_nCH_3$ where n is an integer from 1 to 10, in particular n=1;

$(CF_3)_2CHO(CH_2O)_nCH_2Cl$ where n is an integer from 0 to 10, in particular n=0 or 1; and $(CF_3)_2CHOCHCl_2$.

These precursors may be in the form of mixtures.

In a preferred embodiment of the invention, sevoflurane is prepared according to the reaction sequence depicted in Scheme 1. As described above, conducting this reaction sequence can lead to generation of HFIP hydrolyzable precursors, in addition to the desired sevoflurane. In particular, the conversion of sevomethyl ether into chlorosevo leads to a mixture of unreacted sevomethyl ether, chlorosevo and other HFIP hydrolyzable precursors. Isolation of chlorosevo from the mixture can be achieved by any purification procedure well-known to those of skill in the art that provides a chlorosevo-depleted mixture in addition to the purified chlorosevo. For example, a distillation procedure can be used. When the isolation procedure includes a distillation procedure, the isolated chlorosevo can be collected in distillation fractions, while the chlorosevo-depleted mixture can remain in the stillpot. The chlorosevo-depleted mixture typically contains, in addition to undistilled chlorosevo, other HFIP hydrolyzable precursors including small proportions of dichlorosevo, and a number of other high-boiling components which form by thermal or hydrolytic processes that occur during distillation. The composition of the chlorosevo-depleted mixture can vary depending on the distillation process parameters (e.g., stillpot temperature and duration of the process). For example, the proportion of chlorosevo remaining in the mixture can vary depending on the tolerance for the distillation fractions containing the isolated chlorosevo.

Typically, the distillation procedure comprises a fractional distillation procedure wherein fractions of a specified purity of chlorosevo are collected and combined. The distillation can be conducted so that unreacted sevomethyl ether can be collected, in addition to chlorosevo. Preferably, the distillation conducted is a fractional distillation so that the chlorosevo and sevomethyl ether are isolated in separate distillation fractions. Notably, the recovered sevomethyl ether can be re-utilized as feed for the chlorination reaction.

The chlorosevo-depleted mixture is heated with a strong protic acid, e.g., concentrated sulfuric acid, at a temperature effective to convert the other HFIP hydrolyzable precursors to HFIP. As will be readily apparent to those of skill in the art, any chlorosevo present in the mixture will be hydrolyzed along with the other HFIP hydrolyzable precursors under the reaction conditions to provide additional quantities of HFIP.

As used herein the terms, "strong protic acids" refer to acids that are effective to hydrolyze the HFIP hydrolyzable precursors to provide HFIP. Such acids preferably include sulfuric acid, polyphosphoric acid, benzenesulfonic acid, toluenesulfonic acid and methanesulfonic acid. Manipulating suitable reaction parameters such as raising the reaction pressure to levels higher than atmospheric pressure (using, for example, a pressure vessel), may allow other acids such as hydrochloric acid, phosphoric acid and the like to be used to achieve hydrolysis of the HFIP hydrolyzable precursors.

In a preferred embodiment of the process, the strong protic acid is concentrated sulfuric acid. Preferably, the proportion of concentrated sulfuric acid added relative to the amount of the chlorosevo-depleted mixture is at least 10% by volume of the total hydrolysis mixture (i.e., chlorosevo-depleted mixture and concentrated sulfuric acid), more preferably, the proportion of concentrated sulfuric acid comprises at least 20% by volume.

An attractive feature of the process is that a single charge of sulfuric acid can be reused for hydrolyzing several charges of chlorosevo-depleted mixture without a significant decrease in its hydrolytic effectiveness. This feature significantly reduces the burden of treating the waste stream emanating from the process. For example, strongly acidic aqueous waste streams must typically be neutralized before being further treated, and ultimately discharged. Accordingly, volume reductions in strongly acidic waste streams are particularly desirable for commercial-scale processes.

The hydrolysis of the mixture containing the chlorosevo-depleted mixture and concentrated sulfuric acid can be conducted at atmospheric pressure at a temperature that is preferably 60° C. or more. More preferably, the hydrolysis is conducted at temperatures sufficient to cause reflux of the organic components of the hydrolysis mixture. The hydrolysis can also be performed at lower temperatures by employing longer reaction times, or at a higher temperatures by conducting the process at higher pressure using, for example, a pressure vessel.

The recovery of HFIP from the hydrolysis mixture can be conducted by a number of methods. In a preferred embodiment of the process, the HFIP formed is distilled directly out of the reaction vessel after substantial completion of the hydrolysis reaction (i.e., completion sufficient to provide useful levels of HFIP recovery).

In another preferred embodiment, HFIP is distilled concurrently with the hydrolysis process. In embodiments of the process where the distillation is conducted concurrently with the hydrolysis, a fractionating column can be used to permit distillation of HFIP (and any sevomethyl ether) while returning unreacted chlorosevo and other HFIP hydrolyzable precursors to the reactor. In this embodiment, the recovery process can be conducted as a continuous process, in which HFIP is continuously removed from the reactor by fractional distillation, while additional chlorosevo-depleted mixture is added to the reactor.

In alternative embodiments, the HFIP may be recovered by mixing either the entire contents of the hydrolyzed mixture or separated organic phase with water or other aqueous solutions; followed by a isolation of the purified HFIP by, for example, distillation. Optionally, the acid used in the distillation can be either partially or completely neutralized by diluting the reaction mixture with dilute aqueous base; or by diluting the reaction mixture with water followed by the addition of a base, e.g., sodium hydroxide.

It will be readily apparent to those of skill in the art that chlorosevo-depleted mixtures from several stillpot residues or other sources of HFIP hydrolyzable precursors can be combined, and the hydrolysis with strong protic acid conducted on the combined mixture. Also, two or more batches of hydrolysis mixtures can be combined prior to isolating the recovered HFIP from the other components of the combined hydrolysis mixture. In another embodiment, the aqueous waste stream from the methylation reaction of Scheme 1, which contains quantities of unreacted HFIP, can be combined with the hydrolysis mixture, prior to isolating the HFIP from the other components in the combined mixture.

The recovered HFIP isolated from the hydrolysis mixture can be recycled by reintroducing the HFIP into the first step of the process, i.e., the methylation of the HFIP. The recovered HFIP can be re-introduced alone, or in combination with a fresh charge of HFIP.

The following examples further illustrate the present invention, but of course, should not be construed as in any way limiting its scope.

Gas chromatography was performed under the following conditions: Hewlett-Packard 5890 instrument equipped with a thermal-conductivity detector and ⅛" ID×12' "mixed column" (Supelco Inc., packed with 10% Igepal CO-880 and 15% Ucon LB-550× on 60/80 Chromosorb PAW) using a temperature gradient program from 55° C. to 140° C. at 4° C./min. The structures of the components of the mixtures were determined by $^1$H NMR and GC-MS.

EXAMPLE 1

Hydrolysis of a Chlorosevo-Depleted Mixture Containing HFIP Hydrolyzable Precursors and Recovery of HFIP The chlorination of sevomethyl ether yielded a reaction mixture that was worked up by aqueous extraction followed by distillation to isolate chlorosevo and unreacted sevomethyl ether. The remaining stillpot residue is referred to herein as Mixture A. Gas chromotography (GC) analysis of the Mixture A revealed a complex mixture of halogenated compounds. Identified among these halogenated compounds were chlorosevo (37.3%), dichlorosevo (14.6%), and di-HFIP acetal (32.3%). Mixture A also contained droplets of water and some solid inclusions.

A hydrolysis mixture was prepared by combining equal volumes of Mixture A (65 mL, 100.0 g) and concentrated sulfuric acid (65 mL, 119.6 g). The mixture was kept under reflux for 18 hours. The resulting two-phase, dark-brown reaction mixture was subjected to distillation to provide 66.8 g of a clear liquid, bp 50–63° C. According to GC analysis, this liquid was a mixture of 0.6% of sevomethyl ether, 10.6% of di-HFIP acetal and 88.4% of HFIP.

The distillate was further purified by fractional distillation using 2 ft×½" column filled with glass helices to give a main fraction containing 99+% HFIP (58.8 g, bp 58–59° C.) and a pot residue (8.7 g) containing 89% di-HFIP acetal and 9.7% HFIP.

EXAMPLE 2

Effect of the Proportion of Sulfuric Acid on the Hydrolysis of a Chlorosevo-Depleted Mixture Containing HFIP Hydrolyzable Precursors and the Recovery of HFIP In this example, the effect of the proportion of the strong protic acid, $H_2SO_4$, on the hydrolysis of Mixture A (described in Example 1), and on the recovery of HFIP was evaluated.

In each of 4 trials, Mixture A (100 g) and concentrated sulfuric acid were combined in the volume ratios shown in Table 1. Each of the reaction mixtures in the trials was heated at reflux for 18 hours, and the mixtures were distilled to provide distillates having the weights and composition as shown in Table 1.

TABLE 1

| Trial # | Volume ratio starting Mixture A/ sulfuric acid | Crude Distilled Product, g | Sevomethyl ether % | Di-HFIP acetal % | HFIP % | Unknown % |
| --- | --- | --- | --- | --- | --- | --- |
| 1 | 4:1 | 52.7 | 2.1 | 15.4 | 67.1 | 15.8 |
| 2 | 2:1 | 65.4 | 1.3 | 9.0 | 87.7 | 1.6 |
| 3 | 1:1 | 66.8 | 0.6 | 10.6 | 88.4 | 0 |
| 4 | 1:2 | 67.9 | 0.4 | 5.6 | 93.3 | 0 |

The results in Table 1 demonstrate that higher proportions of sulfuric acid provide higher recoveries of HFIP. However, other factors such as engineering may impact the choice of the preferred proportion of sulfuric acid.

EXAMPLE 3

Evaluation of the Efficiency a Single Charge of Sulfuric Acid in Repeated Hydrolysis Trials In this example, the hydrolytic efficiency of a single charge of sulfuric acid was evaluatd over the course of five trials. In each of the five trials, a fresh 100 g (65 mL) charge of Mixture A (described in Example 1) was used. In trial 1, a fresh charge of concentrated sulfuric acid (65 mL, 119.6 g) was combined with the Mixture A and the resulting mixture was heated at reflux for 18 hours. After distillation of the hydrolyzed mixture, the pot residue was cooled to room temperature, and a fresh charge of Mixture A was added to the pot residue. Heating and recovery of the crude hydrolysis product followed. These iterations were repeated three more times. The weight and composition of the crude distilled product is shown in Table 2.

TABLE 2

| Charge | Pot temp, at which distillation started, °C. | Pot temp, at which distillation was stopped, °C. | Product, g | sevomethyl ether, % | Di-HFIP Acetal, % | HFIP, % | Unknown RT, 12.3 min, % |
|---|---|---|---|---|---|---|---|
| 1 | 85  | 130 | 66.8 | 0.6  | 10.6 | 88.4 | 0   |
| 2 | 96  | 130 | 46.4 | 2.9  | 6.5  | 89.4 | 0.7 |
| 3 | 103 | 135 | 50.1 | 5.2  | 6.6  | 86.9 | 0.8 |
| 4 | 107 | 140 | 52.9 | 6.7  | 8.0  | 84.0 | 0.5 |
| 5 | 107 | 140 | 47.1 | 10.0 | 8.1  | 80.4 | 0.4 |

The results clearly demonstrate that a single charge of sulfuric acid can be used repeatedly to effectively hydrolyze several batches of mixtures containing HFIP hydrolyzable precursors. This feature significantly reduces the volume of spent aqueous acidic waste that must be treated before being discharged.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A process for preparing sevoflurane, comprising:
   (a) treating hexafluoroisopropanol with a reactant selected from paraformaldehyde and 1,3,5-trioxane in the presence of a chlorinating agent to provide chiorosevo and a HFIP hydrolyzable precursor; and treating chiorosevo with a fluoride reagent to give sevoflurane
   (b) separating the HFIP hydrolyzable precursor from the reaction of (a);
   (c) heating the separated HFIP hydrolyzable precursor with a strong protic acid at a temperature effective to convert the HFIP hydrolyzable precursor to HFIP; and
   (d) isolating the recovered HFIP.

2. A process for preparing sevoflurane, comprising:
   (a) treating the HFIP feed with a methylating agent to give sevomethyl ether, chlorinating the sevomethyl ether to give chiorosevo and a HFIP hydrolyzable precursor, and treating chiorosevo with a fluoride reagent to give sevoflurane
   (b) separating the HFIP hydrolyzable precursor from the reaction of (a);
   (c) heating the separated HFIP hydrolyzable precursor with a strong protic acid at a temperature effective to convert the HFIP hydrolyzable precursor to HFIP; and
   (d) isolating the recovered HFIP.

3. A process for preparing chiorosevo from HFIP, comprising: (a) alkylating an HFIP feed to give sevomethyl ether; (b) chlorinating sevomethyl ether to give a mixture comprising chiorosevo and other HFIP hydrolyzable precursors; (c) isolating chiorosevo from the mixture to provide a chlorosevo-depleted mixture; (d) heating the chlorosevo-depleted mixture with a strong protic acid at a temperature effective to convert the other HFIP hydrolyzable precursors to HFIP; and (e) isolating recovered HFIP from the chlorosevo-depleted mixture.

4. The process of claim 3, further comprising: (f) adding the recovered HFIP to the HFIP feed of (a), and repeating (a) through (e).

5. The process of claim 3, further comprising isolating sevomethyl ether from the mixture of (b) or the chlorosevo-depleted mixture of (c).

6. The process of claim 3, wherein the hydrolyzable precursors are selected from one or more of di-HFIP acetal and dichlorosevo.

7. The process of claim 6, wherein the strong protic acid is selected from the group consisting of sulfuric acid, benzenesulfonic acid, toluenesulfonic acid, methanesulfonic acid, hydrochloric acid, phosphoric acid and polyphosphoric acid.

8. The process of claim 7, wherein the strong protic acid is concentrated sulfuric acid.

9. The process of claim 8, wherein in (d), the chlorosevo-depleted mixture is heated with at least 10% by volume of concentrated sulfuric acid.

10. The process of claim 3, wherein the heating of (d) is conducted at atmospheric pressure.

11. The process of claim 10, wherein the temperature at which the chlorosevo-depleted mixture is heated with a strong protic acid is at least 60° C.

12. The process of claim 3, wherein the isolation of chlorosevo in (c) comprises distillation of the mixture, and isolation of distilled chlorosevo.

13. The process of claim 3, wherein the isolation in (c) further comprises isolation of unreacted sevomethyl ether.

14. The process of claim 13, wherein the isolation comprises fractional distillation, and isolation of chlorosevo and unreacted sevomethyl ether in separate distillation fractions.

15. A serial or continuous process of producing chlorosevo by repeating (a) through (f) of claim 4.

* * * * *

UNITED STATES PATENT AND TRADEMARK OFFICE
CERTIFICATE OF CORRECTION

PATENT NO. : 6,987,204 B2
APPLICATION NO. : 10/755850
DATED : January 17, 2006
INVENTOR(S) : Leonid A. Rozov and Ralph A. Lessor It is certified that error appears in the above-identified patent and that said Letters Patent is hereby corrected as shown below:

Col. 9, Claim 1, line 53, change "chiorosevo" to --chlorosevo--

Col. 9, Claim 1, line 54, change "chiorosevo" to --chlorosevo--

Col. 9, Claim 2, line 65, change "chiorosevo", to --chlorosevo--

Col. 10, Claim 3, line 8, change "chiorosevo", to --chlorosevo--

Col. 10, Claim 3, line 11, change "chiorosevo", to --chlorosevo--

Col. 10, Claim 3, line 12, change "chiorosevo", to --chlorosevo--

Signed and Sealed this

Twenty-second Day of August, 2006

JON W. DUDAS
*Director of the United States Patent and Trademark Office*